United States Patent
Li et al.

(10) Patent No.: US 11,607,417 B2
(45) Date of Patent: Mar. 21, 2023

(54) USES OF CELASTROL IN PREVENTING AND/OR TREATING CHOLESTATIC LIVER DISEASE AND LIVER FIBROSIS

(71) Applicants: KUNMING INSTITUTE OF BOTANY, THE CHINESE ACADEMY OF SCIENCES, Kunming (CN); ZHEJIANG CHONGLING TECHNOLOGY CO., LTD., Hangzhou (CN)

(72) Inventors: Fei Li, Kunming (CN); Qi Zhao, Kunming (CN)

(73) Assignees: ZHEJIANG CHONGLING TECHNOLOGY CO., LTD., Zhejiang (CN); KUNMING INSTITUTE OF BOTANY, THE CHINESE ACADEMY OF SCIENCES, Yunnan (CN)

( * ) Notice: Subject to any disclaimer, the term of this patent is extended or adjusted under 35 U.S.C. 154(b) by 508 days.

(21) Appl. No.: 16/494,047

(22) PCT Filed: Mar. 9, 2018

(86) PCT No.: PCT/CN2018/078551
§ 371 (c)(1),
(2) Date: Feb. 17, 2021

(87) PCT Pub. No.: WO2018/166404
PCT Pub. Date: Sep. 20, 2018

(65) Prior Publication Data
US 2021/0186986 A1    Jun. 24, 2021

(30) Foreign Application Priority Data

Mar. 15, 2017    (CN) .......................... 201710151750.2

(51) Int. Cl.
*A61K 31/56*    (2006.01)
(52) U.S. Cl.
CPC .................................... *A61K 31/56* (2013.01)
(58) Field of Classification Search
CPC ............ A61K 31/56; A61K 36/37; A61P 1/16
See application file for complete search history.

(56) References Cited

FOREIGN PATENT DOCUMENTS

| CN | 103524592 A | 1/2014 |
|---|---|---|
| CN | 104095855 A | 10/2014 |
| CN | 105497041 A | 4/2016 |
| CN | 106924265 A | 7/2017 |

OTHER PUBLICATIONS

El-Swefy et al. (Annals of Hepatology, 8(1), 2009, 41-49). (Year: 2009).*
Stedman et al. (PNAS, 2006, 103, 30, 11323-328). (Year: 2006).*
He, W., et al., "Therapeutic Effects of Celastrol on DEN Induced Liver Fibrosis Rats and Its Mechanisms," Chinese Pharmacological Bulletin 29(4):519-524, Apr. 2013.
Sun, P., "Clinical Adverse Reaction Distribution Features of Tripterygium Wilfordii and Its Preparations: A Systematic Review of Randomized Controlled Trials," World Science and Technology-Modernization of Traditional Chinese Medicine 17(9):1899-1905, Sep. 2015.
Tang, N., et al., "Progress of Signal Transduction Pathway in Cholestatic Liver Fibrosis," International Journal of Pediatrics 43(8): 626-630, Sep. 2016.
Zhang, Q., et al., "Mechanisms and Treatment of Cholestasis-Induced Liver Fibrosis," Journal of Clinical Hepatobiliary 31(3):337-341, Mar. 2015.
International Search Report dated Jun. 11, 2018, issued in International Application No. PCT/CN2018/078551, filed Mar. 9, 2018, 9 pages.
Written Opinion dated Jun. 11, 2018, issued in International Application No. PCT/CN2018/078551, filed Mar. 9, 2018, 10 pages.
First Office Action dated Dec. 20, 2018, issued in Chinese Application No. 201710151750.2, filed Mar. 15, 2017, 8 pages.
Second Office Action dated Jul. 16, 2019, issued in Chinese Application No. 201710151750.2, filed Mar. 15, 2017, 11 pages.
Bataller, A. and D.A. Brenner, "Liver Fibrosis," The Journal of Clinical Investigation, 115(2):209-18, Feb. 2005.
Hilscher, M.B., et al., "Cholestatic Liver Diseases: A Primer for Generalists and Subspecialists," Mayo Clinic Proceedings 95(10):2263-2279, Oct. 2020.
Reichel, C. and P.J. Meier Abt, "Cholestatic Liver Diseases," Therapeutische Umschau 54(11):639-44, Nov. 1997, <https://pubmed.ncbi.nlm.nih.gov/9454366/>, Abstract.
Zhang, Y. and Y. Zhang, "Clinical Efficacy Analysis of Ursodeoxycholic Acid in the Treatment of Cholestatic Drug-Induced Liver Injury in the Elderly," Liver 18(10):685-687, Oct. 2013.

* cited by examiner

*Primary Examiner* — Umamaheswari Ramachandran
(74) *Attorney, Agent, or Firm* — Christensen O'Connor Johnson Kindness

(57) ABSTRACT

The present disclosure relates to a celastrol or a pharmaceutically acceptable salt thereof, and a use thereof in the manufacture of a medicament for preventing and/or treating a cholestatic liver disease or a liver fibrosis.

4 Claims, 9 Drawing Sheets

USES OF CELASTROL IN PREVENTING AND/OR TREATING CHOLESTATIC LIVER DISEASE AND LIVER FIBROSIS

CROSS-REFERENCES TO RELATED APPLICATIONS

This application is a National Stage of International Application No. PCT/CN2018/078551, filed Mar. 9, 2018, which claims priority to Chinese Application No. 201710151750.2, filed Mar. 15, 2017, the disclosures of which are incorporated herein by, reference in their entirety.

TECHNICAL FIELD

The present disclosure belongs to the field of cholestasis drugs and liver fibrosis drugs, and in particular relates to a use of a celastrol or a pharmaceutically acceptable salt thereof in manufacture of a medicament for preventing and/or treating a cholestatic liver disease or a liver fibrosis, further to a method for prevention and/or treatment of a cholestatic liver disease or a liver fibrosis, and further to a celastrol or a pharmaceutically acceptable salt thereof for use in prevention and/or treatment of a cholestatic liver disease or a liver fibrosis.

BACKGROUND ART

The most fundamental cause of cholestasis is the accumulation of a large amount of toxic bile acids in liver cells, and thus cholestasis is a disorder in the liver. If cholestasis is not treated timely, it may lead to liver fibrosis, cirrhosis, liver failure, and even death. Cholestasis is divided into extrahepatic cholestasis and intrahepatic cholestasis. Extrahepatic cholestasis is caused by diseases such as biliary tumor, cyst, and culculus of bile duct. Intrahepatic cholestasis is caused by sepsis, drugs, primary biliary cirrhosis, primary sclerosing cholangitis, viral hepatitis, alcoholic liver, pregnancy and so on. In addition, there are many genetically induced progressive familial intrahepatic cholestasis (PFIC). To date, ursodeoxycholic acid (UDCA) and obeticholic acid (OCA) are the only two drugs approved by the US Food and Drug Administration (FDA) for treatment of cholestatic liver disease. UDCA is effective in the treatment of phase I and phase II primary biliary cirrhosis (PBC), but UDCA is not good in the treatment of primary sclerosing cholangitis (PSC), and many patients have tolerance problem with long-term monotherapy with UDCA, so its use is still controversial. OCA was approved by FDA in 2016 for the treatment of cholestatic liver disease, and the side effects of this drug have not been fully understood. At present, the most common side effects of OCA include skin itching and fatigue. At present, a large number of patients in clinical practice are in urgent need of drug treatment for cholestatic liver disease, but the approved liver-protecting drugs or drugs for treating liver diseases are rare or unreliable, and tens of thousands of patients with cholestatic liver disease cannot receive effective drug treatment. Liver transplantation can significantly improve the survival rate of patients, but the safety of this transplant operation depends to a large extent on the regenerative capacity of the patient's residual liver, and thus it is only suitable for patients with advanced liver disease or acute liver failure. Therefore, the development of drugs for the treatment of cholestatic liver disease is an imminent need.

Liver fibrosis refers to the phenomenon that the extracellular matrix and connective tissue proliferate abnormally after the cells are damaged. In the process of development of various chronic liver diseases into liver cirrhosis, liver fibrosis is an inevitable pathological stage, which has a high incidence rate of about 100/100,000 people. Liver fibrosis is a clinically reversible lesion, while cirrhosis and liver cancer are irreversible lesions with high mortality. Therefore, controlling the occurrence and development of liver fibrosis can effectively reduce the occurrence of liver cirrhosis and liver cancer.

The traditional Chinese medicine *Tripterygium wilfordii* is the root of *Tripterygium wilfordii* Hook.f. in the family Celastraceae, also called Huang-teng, Huang-la-teng, Cai-chong-yao, Hong-yao and Shui-mang-cao, mainly produced in Fujian, Anhui, Zhejiang, Henan and other places in China, and often used for treating diseases such as arthritis, leprosy, eczema, tuberculosis. Celastrol (also called Tripterine) is an important triterpenoid active ingredient in the traditional Chinese medicine *Tripterygium wilfordii*, and is widely present in celastraceae plants such as *Tripterygium wilfordii* Hook.f., *Celastrus orbiculatus* Thunb., and *Celastrus monospermus* Roxb. Celastrol has demonstrated good biological activity in researches of anti-inflammation, immunosuppression, anti-tumor, anti-neurodegeneration and weight loss, and has broad development prospects. However, the application of celastrol in the treatment of cholestatic liver disease and liver fibrosis has not been reported so far.

Contents of the Invention

The inventors have unexpectedly found that celastrol can be used for the prevention and/or treatment of cholestatic liver disease and liver fibrosis, and showed remarkable effects.

The present disclosure relates to a use of celastrol or a pharmaceutically acceptable salt thereof in manufacture of a medicament for preventing and/or treating a cholestatic liver disease.

The present disclosure relates to a use of celastrol or a pharmaceutically acceptable salt thereof in manufacture of a medicament for preventing and/or treating a liver fibrosis.

The present disclosure also relates to a use of a pharmaceutical composition in manufacture of a medicament for preventing and/or treating a cholestatic liver disease or a liver fibrosis, wherein the pharmaceutical composition comprises celastrol or a pharmaceutically acceptable salt thereof, and a pharmaceutically acceptable adjuvant or excipient.

The present disclosure also relates to a method for prevention and/or treatment of a cholestatic liver disease or a liver fibrosis, the method comprising administering to a patient in need thereof a therapeutically effective amount of celastrol or a pharmaceutically acceptable salt thereof, or the method comprising administering to a patient in need thereof a therapeutically effective amount of a pharmaceutical composition, wherein the pharmaceutical composition comprises celastrol or a pharmaceutically acceptable salt thereof, and a pharmaceutically acceptable adjuvant or excipient.

The present disclosure also relates to celastrol or a pharmaceutically acceptable salt thereof, for use in the prevention and/or treatment of a cholestatic liver disease or a liver fibrosis.

The present disclosure also relates to a pharmaceutical composition, for use in the prevention and/or treatment of a cholestatic liver disease or a liver fibrosis, wherein the pharmaceutical composition comprises celastrol or a pharmaceutically acceptable salt thereof, and a pharmaceutically acceptable adjuvant or excipient.

In some embodiments, the cholestatic liver disease of the present disclosure is a chemical substance-induced cholestatic liver disease, a drug-induced cholestatic liver disease, or a primary cholestatic liver disease.

In some embodiments, the cholestatic liver disease of the present disclosure is a cholestatic liver disease caused by excessive estrogen in vivo.

In some embodiments, the liver fibrosis of the present disclosure is a chemical substance-induced liver fibrosis, a drug-induced liver fibrosis, a hepatitis B-induced liver fibrosis, or a hepatitis C-induced liver fibrosis.

In some embodiments, the pharmaceutical compositions of the present disclosure may also optionally further comprise one or more additional pharmaceutically active compounds.

In some embodiments, the celastrol or a pharmaceutically acceptable salt thereof of the present disclosure may be used alone as an active ingredient for the prevention and/or treatment of a cholestatic liver disease or a liver fibrosis, or be used in combination with an additional pharmaceutically active compound for the prevention and/or treatment of a cholestatic liver disease or a liver fibrosis.

In some embodiments, the celastrol or a pharmaceutically acceptable salt thereof of the present disclosure decreases various bile acid components (e.g., ω-MCA, DCA, TβMCA/TαMCA, TCA, THDCA/TUDCA, TCDCA, TDCA) in a patient's plasma, or reduces liver injury or liver necrosis caused by cholestasis, or inhibits or alleviates inflammation caused by cholestasis.

The additional pharmaceutically active compound of the present disclosure exemplarily includes ursodeoxycholic acid (UDCA), obeticholic acid (OCA), and S-adenosylmethionine and the like.

In some embodiments, the celastrol or a pharmaceutically acceptable salt thereof or the pharmaceutical composition of the present disclosure can be administered by, for example, oral or parenteral route. The celastrol or a pharmaceutically acceptable salt thereof or the pharmaceutical composition of the present disclosure can be prepared into various preparation forms according to conventional methods in the art, including but not limited to tablets, capsules, solutions, suspensions, granules, injections or the like, which can be administered by, for example, oral or parenteral route.

It should be further noted that the dosage and usage of the celastrol or a pharmaceutically acceptable salt thereof according to the present disclosure depends on various factors, including age, weight, gender, natural health status, nutritional status, activity intensity of compound, time of administration, rate of metabolism, severity of disease condition, and subjective judgment of physician who makes diagnosis and give treatment. A preferred dosage is between 0.01 and 1000 mg/kg body weight/day.

In some embodiments, when the celastrol or a pharmaceutically acceptable salt thereof of the present disclosure is used for the prevention and/or treatment of a cholestatic liver disease, the oral administration is preferred. In some embodiments, a patient with a cholestatic liver disease is orally administrated with an dose between about 0.005 mg and about 500 mg per kilogram of body weight per day, more preferably between about 0.05 mg and about 100 mg per kilogram of body weight per day, and most preferably between about 0.1 mg and about 10 mg per kilogram of body weight per day.

In some embodiments, when the celastrol or a pharmaceutically acceptable salt thereof of the present disclosure is used for the prevention and/or treatment of a liver fibrosis, the oral administration is preferred. In some embodiments, a patient with a liver fibrosis is orally administrated with an dose between about 0.005 mg and about 500 mg per kilogram of body weight per day, more preferably between about 0.05 mg and about 100 mg per kilogram of body weight per day, and most preferably between about 0.1 mg and about 10 mg per kilogram of body weight per day.

The celastrol is extracted from *Tripterygium wilfordii* Hook.f. in the genus *Tripterygium* of the family Celastraceae, and has a structure as follows:

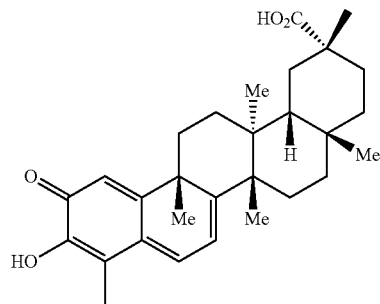

The celastrol of the present disclosure may be used either as itself or as a pharmaceutically acceptable salt thereof. The pharmaceutically acceptable salt of celastrol includes a salt of celastrol formed with a pharmaceutically acceptable inorganic or organic acid, or a pharmaceutically acceptable inorganic or organic base. Examples of exemplary pharmaceutically acceptable salt include salts of celastrol formed with hydrochloric acid, hydrobromic acid, sulfuric acid, phosphoric acid, nitric acid, perchloric acid, fumaric acid, acetic acid, propionic acid, succinic acid, glycolic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluenesulfonic acid, methanesulfonic acid, naphthalene-2-sulfonic acid, benzenesulfonic acid, hydroxynaphthoic acid, hydroiodic acid, malic acid, tannic acid, etc., or include salts of celastrol formed with sodium, lithium, potassium, magnesium, aluminum, calcium, zinc, N,N'-dibenzylethylenediamine, chloroprocaine, choline, diethanolamine, ethylenediamine, N-methylglucamine, procaine, etc.

In the present disclosure, the "pharmaceutically acceptable salt" refers to a salt that retains the desired biological activity of the target compound and exhibits minimal undesired toxicological effect. These pharmaceutically acceptable salts can be prepared in situ during the final isolation and purification of the compound or by separately reacting the purified compound in its free acid or free base form with a suitable base or acid.

The mechanism of action of the celastrol or a pharmaceutically acceptable salt thereof in the prevention and/or treatment of cholestasis according to the present disclosure is that the celastrol plays a role by regulating the expression of sirtuin 1 (SIRT1), and the expression of farnesoid X receptor (FXR). SIRT1 is a highly conserved NAD$^+$-dependent protein deacetylase, and plays an important role in gene silencing, cell life, and metabolic regulation. SIRT1 can regulate many important nuclear receptors, such as FXR, peroxisome proliferator-activated receptor α (PPARα), and peroxisome proliferator-activated receptor γ (PPARγ), either directly or indirectly through its acetylation. FXR is closely related to bile acid homeostasis and is the most important cholic acid regulatory gene, can regulate a variety of bile acid synthesis genes, such as CYP7A1 and CYP8B1, and can also regulate a variety of bile acid transport genes and detoxification genes. Therefore, in this study, it is believed that celastrol can protect the liver from damage through the SIRT1-FXR signal pathway. Celastrol decreases the formation of bile acids in vivo by inhibiting the synthesis genes of bile acid, such as CYP7A1 and CYP8B1, thereby inhibiting the further synthesis of bile acid from the source. By regulating genes such as CYP3A4, SULT2A1, UGT2B4, UGT2B7 to promote the detoxification of bile acid, the content of harmful bile acids can also be reduced. In addition, celastrol can decrease the bile acid entering the liver by inhibiting the expression of bile acid absorption transporters (such as Ntcp, Oatp1, Oatp4), and promote bile acid excretion by increasing the expression of bile acid efflux transporters (such as Ostβ, Mrp4, Bsep, and Mrp2), thereby to achieve the treatment of a cholestatic liver disease.

In the present disclosure, by using ANIT- and TAA-induced mouse cholestasis liver injury models, it is studied and confirmed that celastrol can be used for prevention and/or treatment of cholestatic liver injury, can significantly decrease various bile acid components in plasma, thereby significantly reducing liver injury and liver necrosis caused by cholestasis, significantly inhibiting inflammation caused by cholestasis, and showing significant therapeutic effect on cholestasis. In addition, when inducing liver fibrosis in mice by long-term administration of TAA, we have found that celastrol could treat liver fibrosis and is promising to be developed as a new anti-liver fibrosis drug.

BRIEF DESCRIPTION OF DRAWINGS

The drawings described herein are provided for further understanding of the present disclosure, which is a part of the present disclosure, and the exemplary examples of the present disclosure and the description thereof are for illustrating the present disclosure and do not constitute an undue limitation of the disclosure. In the drawings:

FIGS. 1A to 1E show the prevention and/or protection effects of celastrol by intragastric administration on the ANIT-induced cholestatic liver injury, wherein: FIG. 1A shows mouse liver tissue section of the blank group; FIG. 1B shows mouse liver tissue pathological section of the ANIT model group; FIG. 1C shows mouse liver tissue pathological slices of the treatment group; FIG. 1D shows a histogram of the relative content changes of various bile acid components in mouse plasma, including cholic acid (CA), deoxycholic acid (DCA), tauro-β-muricholic acid/tauro-α-muricholic acid (TβMCA/TαMCA), taurocholic acid (TCA), and taurohyodeoxycholic acid/tauroursodeoxycholic acid (THDCA/TUDCA); FIG. 1E shows a histogram of the relative content changes of various bile acid components in mouse liver, including ω-muricholic acid (ω-MCA), β-muricholic acid (β-MCA), cholic acid (CA), deoxycholic acid (DCA), tauro-β-muricholic acid/tauro-α-muricholic acid (TβMCA/TαMCA), taurocholic acid (TCA), glycocholic acid (GCA), taurolithocholic acid (TLCA). In FIGS. 1A to 1E, n=6 mice/group, by Student's t-test, as comparing the model group with the blank group, *P<0.05; P<0.01; *P<0.001; as comparing the treatment group with the model group, #P<0.05; ##P<0.01; ###P<0.001.

FIGS. 2A to 2E show the prevention and/or protection effects of celastrol by intragastric administration on the TAA-induced cholestatic liver injury, wherein: FIG. 2A shows mouse liver tissue section of the blank group; FIG. 2B shows mouse liver tissue pathological section of the TAA model group; FIG. 2C shows mouse liver tissue pathological section of the treatment group; FIG. 2D shows a histogram of the relative content changes of various bile acid components in mouse plasma, including ω-muricholic acid (ω-MCA), deoxycholic acid (DCA), tauro-β-muricholic acid/tauro-α-muricholic acid (TβMCA/TαMCA), taurocholic acid (TCA), taurohyodeoxycholic acid/tauroursodeoxycholic acid (THDCA/TUDCA), taurochenodeoxycholic acid (TCDCA), taurodeoxycholic acid (TDCA); FIG. 2E shows a histogram of the relative content changes of various bile acid components in mouse liver, including ω-muricholic acid (ω-MCA)), β-muricholic acid (β-MCA), cholic acid (CA), deoxycholic acid (DCA), tauro-β-muricholic acid/tauro-α-muricholic acid (TβMCA/TαMCA), taurocholic acid (TCA), glycocholic acid (GCA), taurolithocholic acid (TLCA). In FIGS. 2A to 2E, n=6 mice/group, by Student's t-test, as comparing the model group with the blank group, *P<0.05; P<0.01; *P<0.001; as comparing the treatment group with the model group, #P<0.05; ##P<0.01; ###P<0.001.

FIGS. 3A to 3F show that under the condition of SIRT1 inhibition, the prevention and/or protection effects of celastrol by intragastric administration on ANIT-induced cholestatic liver injury are weakened, wherein: FIG. 3A shows mouse liver tissue section of the blank group; FIG. 3B shows mouse liver tissue pathological section of the ANIT model group; FIG. 3C shows mouse liver tissue pathological section of the treatment group; FIG. 3D shows mouse liver tissue pathological section of the EX527 group; FIG. 3E shows a histogram of plasma biochemical indicators, including levels of aspartate aminotransferase (AST), alanine aminotransferase (ALT), alkaline phosphatase (ALP); FIG. 3F shows a histogram of the relative content changes of various bile acid components in mouse plasma, including cholic acid (CA), deoxycholic acid (DCA), tauro-β-muricholic acid/tauro-α-muricholic acid (TβMCA/TαMCA), taurocholic acid (TCA), and taurohyodeoxycholic acid/tauroursodeoxycholic acid (THDCA/TUDCA). In FIGS. 3A to 3F, n=6 mice/group, by Student's t-test, as comparing the model group with the blank group, *P<0.05; P<0.01; *P<0.001; as comparing the treatment group with the model group, #P<0.05; ##P<0.01; ###P<0.001; as comparing the EX527 group with the treatment group, &P<0.05.

FIGS. 4A to 4F show that under the condition of SIRT1 inhibition, the prevention and/or protection effects of celastrol by intragastric administration on TAA-induced cholestatic liver injury are weakened, wherein: FIG. 4A shows mouse liver tissue section of the blank group; FIG. 4B shows mouse liver tissue pathological section of the TAA model group; FIG. 4C shows mouse liver tissue pathological section of the treatment group; FIG. 4D shows mouse liver tissue pathological section of the EX527 group; FIG. 4E shows a histogram of plasma biochemical indicators, including levels of aspartate aminotransferase (AST), alanine aminotransferase (ALT), alkaline phosphatase (ALP); FIG. 4F shows a histogram of the relative content changes of various bile acid components in mouse plasma, including ω-muricholic acid (ω-MCA), deoxycholic acid (DCA), tauro-β-muricholic acid/tauro-α-muricholic acid (TβMCA/TαMCA), taurocholic acid (TCA), taurohyodeoxycholic acid/tauroursodeoxycholic acid (THDCA/TUDCA), taurochenodeoxycholic acid (TCDCA), taurodeoxycholic acid (TDCA). In FIGS. 4A to 4F, n=6 mice/group, by Student's t-test, as comparing the model group with the blank group, *P<0.05; P<0.01; *P<0.001; as comparing the treatment group with the model group, #P<0.05; ##P<0.01;

P<0.001; as comparing the EX527 group with the treatment group, &P<0.05; $$P<0.01; &&&P<0.001.

Figure 5A:
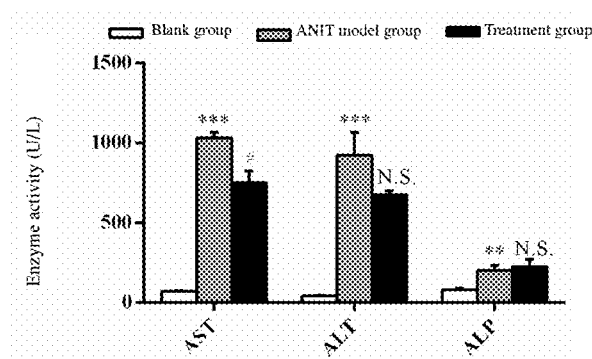
Figure 5B:
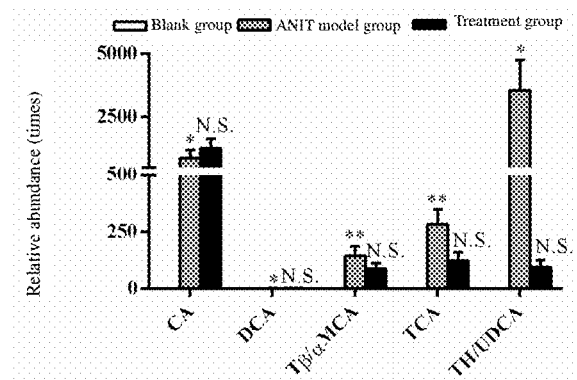

FIGS. 5A and 5B show that under the FXR knockout condition, the prevention and/or protection effects of celastrol by intragastric administration on ANIT-induced cholestatic liver injury are weakened, wherein FIG. 5A shows a histogram of plasma biochemical indicators, including levels of aspartate aminotransferase (AST), alanine aminotransferase (ALT), alkaline phosphatase (ALP); FIG. 5B shows a histogram of the relative content changes of various bile acid components in mouse plasma, including cholic acid (CA), deoxycholic acid (DCA), tauro-β-muricholic acid/tauro-α-muricholic acid (TβMCA/TαMCA), taurocholic acid (TCA), and taurohyodeoxycholic acid/tauroursodeoxycholic acid (THDCA/TUDCA). In FIGS. 5A and 5B, n=6 mice/group, by Student's t-test, as comparing the model group with the blank group, *P<0.05; P<0.01; *P<0.001; as comparing the treatment group with the model group, $^{N.S.}$P>0.05; #P<0.05.

Figure 6A:
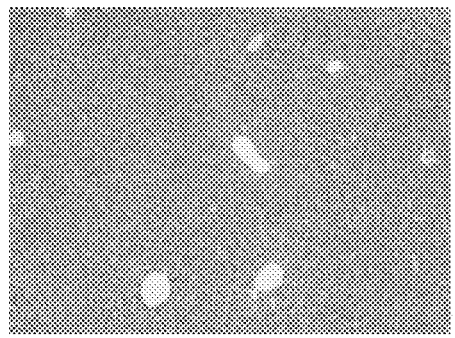
Figure 6B:
Figure 6C:
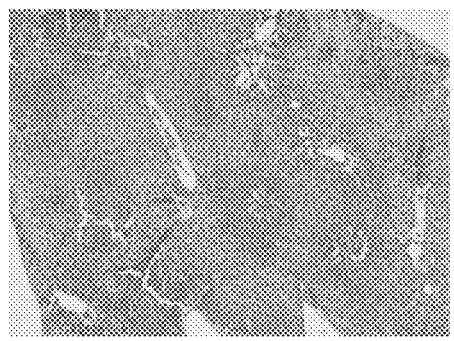
Figure 6D:
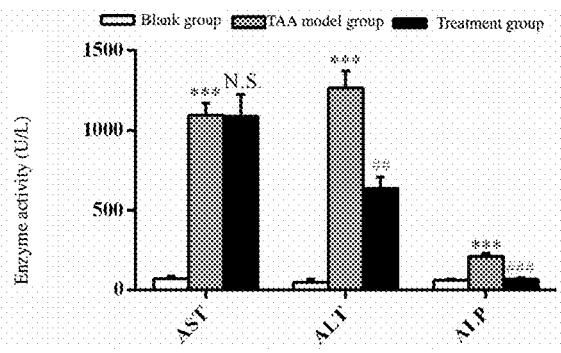
Figure 6E:
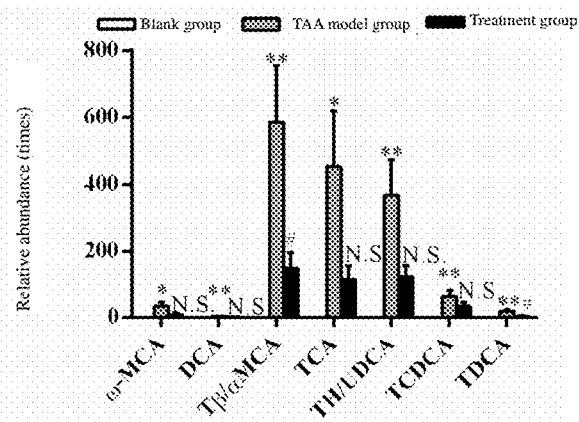

FIGS. 6A to 6E show that under the FXR knockout condition, the prevention and/or protection effects of celastrol by intragastric administration on TAA-induced cholestatic liver injury are weakened, wherein: FIG. 6A shows mouse liver tissue section of the blank group; FIG. 6B shows mouse liver tissue pathological section of the TAA model group; FIG. 6C shows mouse liver tissue pathological section of the treatment group; FIG. 6D shows a histogram of plasma biochemical indicators, including levels of aspartate aminotransferase (AST), alanine aminotransferase (ALT), alkaline phosphatase (ALP); FIG. 6E shows a histogram of the relative content changes of various bile acid components in mouse plasma, including ω-muricholic acid (ω-MCA), deoxycholic acid (DCA), tauro-β-muricholic acid/tauro-α-muricholic acid (TβMCA/TαMCA), taurocholic acid (TCA), taurohyodeoxycholic acid/tauroursodeoxycholic acid (THDCA/TUDCA), taurochenodeoxycholic acid (TCDCA), taurodeoxycholic acid (TDCA). In FIGS. 6A to 6E, n=6 mice/group, by Student's t-test, as comparing the model group with the blank group, *P<0.05; P<0.01; *P<0.001; as comparing the treatment group with the model group, $^{N.S.}$P>0.05; #P<0.05; ##P<0.01; ###P<0.001.

Figure 7A:
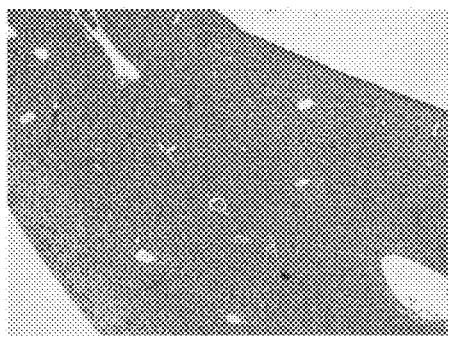
Figure 7B:
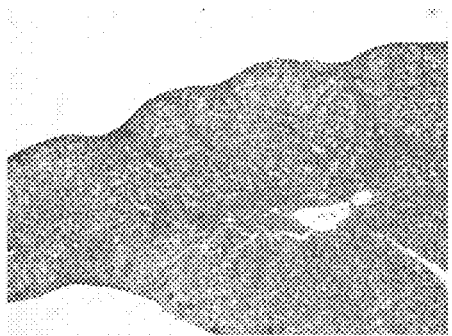
Figure 7C:
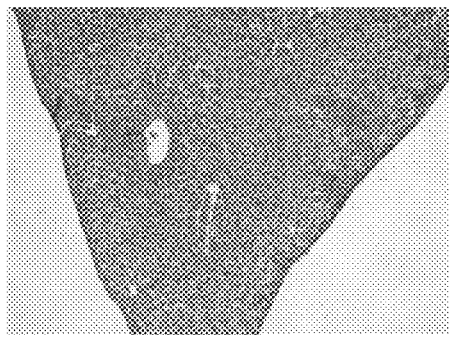
Figure 7D:
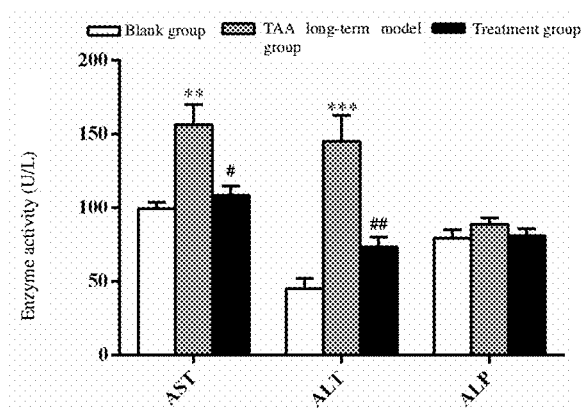

FIGS. 7A to 7D show the prevention and/or protection effects of celastrol by intragastric administration on liver fibrosis induced by long-term administration of TAA in mice, wherein: FIG. 7A shows mouse liver tissue section of the blank group; FIG. 7B shows mouse liver tissue pathological section of the TAA liver fibrosis group; FIG. 7C shows mouse liver tissue pathological section of the treatment group; FIG. 7D shows a histogram of plasma biochemical indicators, including levels of aspartate aminotransferase (AST), alanine aminotransferase (ALT), alkaline phosphatase (ALP). In FIGS. 7A to 7D, n=10 mice per group, by Student's t-test, as comparing the model group with the blank group, P<0.01; *P<0.001; as comparing the treatment group with the model group, #P<0.05; ##P<0.01.

SPECIFIC MODELS FOR CARRYING OUT THE INVENTION

The substantive content of the present disclosure will be illustrated in detail by reference to the following specific examples of the present disclosure. It is understood that the following examples are only intended to illustrate the disclosure, but are not intended to limit the scope of the disclosure. When the specific conditions are not indicated in the Examples, the Examples are carried out under conventional conditions or the conditions recommended by the manufacturers. The drugs or reagents used herein, the manufacturers of which are not indicated, are the all conventional products that are commercially available.

Although many materials and operational methods used in the following examples are well known in the art, the present disclosure still describes them in detail as far as possible. It would be apparent to those skilled in the art that the materials and operation methods used in the following examples are well known in the art unless otherwise stated.

Example 1: Protection and/or Prevention Effects of Celastrol on ANIT-Induced Mouse Cholestatic Liver Injury

1.1 Experimental Animals

C57BL/6 Mice, SPF Grade, Body Weight 20~23 g, Male; Certificate Number: SCXK (Xiang) 2013-0004, purchased from Hunan SJA Laboratory Animal Co., Ltd.

1.2 Drugs and Reagents

Celastrol, red amorphous crystalline powder, purchased from Chengdu Ruifensi Biotechnology Co., Ltd., Lot number: L-003-150420.

Aspartate aminotransferase (AST) kit (Cat. No. C010-3, Lot No. 20161031), alanine aminotransferase (ALT) kit (Cat. No. C009-3, Lot No. 20161031), and alkaline phosphatase (ALP) kit (Cat. No. A059-3, Lot No. 20161031), produced by Nanjing Jiancheng Bioengineering Institute.

α-Naphthyl isothiocyanate (ANIT, Cat. No. N4525-10G, Lot No. 101734146), DMSO (Cat. No. V900090-500m1, Lot No. 101669350), Tween 80 (Cat. No. P1754-500m1, Lot No. 101761909), Formic Acid (Cat. No. 94318-250m1-F, Lot No. 101721592), chlorpropamide (Cat. No. C1290-25G, Lot No. 1002213299), cholic acid (CA, Cat. No. C1129-25G), deoxycholic acid (DCA, Cat. No. D2510-10G), taurocholic acid (TCA, Cat. No. T4009-1G), glycocholic acid (GCA, Cat. No. G2878-500MG), taurohyodeoxycholic acid (THDCA, Cat. No. T0682-250MG) and taurolithocholic acid (TLCA, Cat. No. T7515-100MG), purchased from Sigma Co.

Corn oil (Cat. No. C116025-500G, Lot No. 11524089), purchased from Aladdin Co.

Chromatographic grade acetonitrile (Cat. No. 1.00030.4008), purchased from Merck Co.

ω-muricholic acid (ω-MCA, Cat. No. sc-396738) and tauro-β-muricholic acid (TβMCA, Cat. No. SC-361829), purchased from Santa Cruz Co.

Tauroursodeoxycholic acid (TUDCA, Cat. No. HY-19696A), purchased from MCE Co.

β-muricholic acid (β-MCA, Cat. No. C008852) and tauro-α-muricholic acid (TαMCA, Cat. No. C1893-000), purchased from Steraloids Co.

1.3 Main Instruments

Precision electronic balance, purchased from Sartorius Co.

Automatic microplate reader, purchased from BioTek Instruments Co.

SHA-C water bath constant temperature shaker, purchased from Changzhou Zhongcheng Instrument Manufacturing Co., Ltd.;

Refrigerated centrifuge, purchased from Eppendorf Co.

Ultra-Performance Liquid Chromatography Quadrupole Time-of-Flight Mass Spectrometry, including 1290 sample injector, 1290 pump, column oven, XDB-C18 column (2.1× 100 mm, 1.8 μM), and 6530 quadrupole time-of-flight mass spectrometry, purchased from Agilent Co.

Precellys 24 tissue homogenizer, purchased from Bertin Technologies; upright microscope, purchased from Nikon Co.

Tissue microtome, purchased from Leica Co.

1.4 Experimental Methods

1.4.1 Experimental Grouping

A total of 18 male C57BL/6 mice were divided into three groups: blank group (n=6); model group (n=6); treatment group (n=6).

1.4.2 Preparation and Dosage of Drug Solution

Celastrol was dissolved in a solvent to obtain a celastrol solution at a concentration of 2 mg/mL, wherein the solvent consisted of 1% DMSO, 2% Tween 80, and 97% water (v:v:v). For intragastrical administration, the dosage of celastrol was 10 mg/kg·d. ANIT was dissolved in corn oil to obtain a corn oil solution of ANIT at a concentration of 15 mg/mL, and the dosage of ANIT for intragastrical administration was 75 mg/kg.

1.4.3 Experimental Procedure

The treatment group was intragastrically administered with the celastrol solution at a dosage of 10 mg/kg·d for five consecutive days. At the same time, the blank group and the model group were intragastrically administered with the same dosage of a solvent, wherein the solvent consisted of 1% DMSO, 2% Tween 80 and 97% water (v:v:v), and the solvent was administrated for five consecutive days.

On the third day of administration, ANIT model was established. 4 Hours after administration with the solvent or celastrol solution, the model group and the treatment group were respectively intragastrically administered with the ANIT corn oil solution to induce cholestatic liver injury at a dosage of 75 mg/kg for single administration, and the blank group was fed with an equal dosage of corn oil. After the model was established, the treatment group was continuously administrated with the celastrol solution, and the blank group and the model group was continuously administrated with the same dosage of solvent.

48 Hours after the model was established, the mice were sacrificed by $CO_2$ anesthesia, and mouse livers and plasma samples were taken. The eyeballs of the mice were taken for blood collection. The plasma samples were placed on ice for 1-2 hours, centrifuged at 4000 g for 5 minutes at 4° C., and the supernatant was taken to determine the plasma biochemical indicators, the levels of ALT, AST and ALP.

At the same time, plasma samples were prepared: 10 μL of plasma sample was taken, mixed with 190 μL of 67% (v/v) acetonitrile (containing 5 μM internal standard chlorpropamide), centrifuged at 18000 g for 20 minutes at 4° C., and the supernatant was taken for sample injection.

Liver samples were prepared: 100 mg of liver samples were mixed well with 1 mL of 50% (v/v) acetonitrile (containing 5 μM internal standard chlorpropamide), shaken for 20 minutes at room temperature, and then centrifuged at 18000 g for 20 minutes at 4° C. Thereafter, 200 μL of the supernatant was taken and added with 200 μL of pure acetonitrile, vortexed for 1 minute, centrifuged at 18000 g for 20 minutes at 4° C., and the supernatant was taken for sample injection.

The liquid chromatography conditions were as follows: the injection volume was 5 μL; the column temperature was 45° C.; the flow rate of mobile phase was 0.3 mL/min; the gradient elution was that acetonitrile concentration changed from 2% to 98% during 16 minutes of operation, wherein the mobile phase (water/acetonitrile solution) contained 0.01% formic acid. The elution procedure was as follows: during $0\text{-}12^{th}$ minute, the acetonitrile concentration changed from 2% to 98% at a constant rate; during $12\text{-}14^{th}$ minute, the acetonitrile concentration was maintained at 98%; during $14\text{-}14.1^{th}$ minute, the acetonitrile concentration changed from 98% to 2%; during $14.1\text{-}16^{th}$ minute, the acetonitrile concentration was maintained at 2%. Mass spectrometry conditions were as follows: the temperature of dry gas was 350° C., the pressure of nebulizer was 35 psi, and the voltage of capillary was 3.5 kV.

Part of the collected mouse liver tissue was fixed overnight in formalin and tissue sections were stained with hematoxylin and eosin (H&E).

1.5 Experimental Results

Figure 1A:
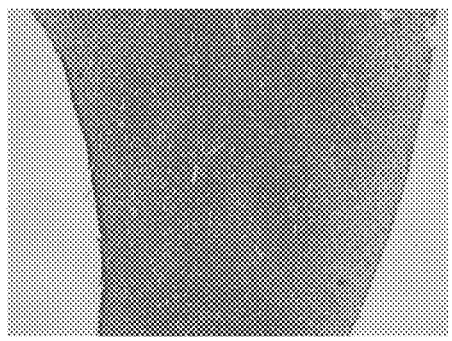
Figure 1B:
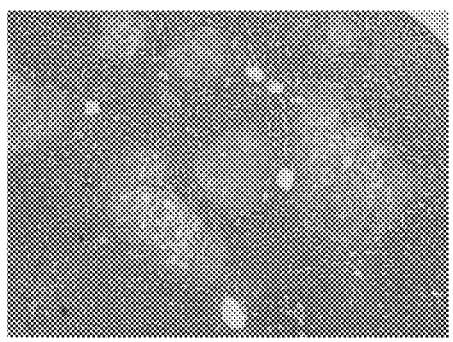
Figure 1C:

The H&E staining results of mouse liver tissues of each group were shown in FIG. 1A, FIG. 1B and FIG. 1C. The results showed that the mouse liver tissue of the blank group had no damage, a severe inflammatory infiltration and a periportal hemorrhage occurred in the mouse liver tissue of the model group, and the mouse liver tissue of the treatment group had no obvious damage. The results showed that celastrol could significantly inhibit the severe inflammatory infiltration and periportal hemorrhage induced by ANIT.

The changes in body weight and liver weight of mouse in each group were shown in Table 1. The results showed that the mice in the blank group, the model group and the treatment group had uniform body weight, and there was no significant difference. However, when the mice were sacrificed, the liver weight (1.22 g) of the model group was significantly higher than that (1.00 g) of the blank group, and the liver weight/body weight ratio (5.78%) of the model group was significantly higher than that (4.56%) of the blank group, indicating the ANIT model group had severe liver injury. When the mice were sacrificed, the liver weight (1.01 g) of the treatment group was significantly lower than that (1.22 g) of the model group, and there was no significant difference in comparison with the mice of the blank group; and the liver weight/body weight ratio (4.66%) of the treated group was significantly lower than that (5.78%) of the model group, and there was no significant difference in comparison with the blank group, indicating that celastrol could significantly inhibit the increases in mouse liver weight and liver weight/body weight ratio induced by ANIT.

TABLE 1

Changes in body weight and liver weight of mouse in each group

| Group | Body weight of mouse when sacrificed (g) | Liver weight of mouse when sacrificed (g) | Liver weight/body weight (%) |
|---|---|---|---|
| Blank group | 21.02 ± 0.94 | 1.00 ± 0.03 | 4.56 ± 0.10 |
| ANIT model group | 21.03 ± 0.94 | 1.22 ± 0.04** | 5.78 ± 0.12** |
| Treatment group | 21.63 ± 1.15 | 1.01 ± 0.05## | 4.66 ± 0.23## |

Note: as comparing the model group with the blank group, **$P < 0.01$; as comparing the treatment group with the model group, ##$P < 0.01$.

The changes of AST, ALT and ALP in mouse plasma of each group were shown in Table 2. The results showed that the levels of AST, ALT and ALP in plasma of the model group were significantly higher than those of the blank group (P<0.01), indicating that the liver tissue of the model group was severely damaged. The levels of AST, ALT and ALP of the treatment group were significantly lower than those of the model group (P<0.01), and there was no significant difference in comparison with the blank group, indicating that celastrol could significantly inhibit the increases of AST, ALT and ALP levels in plasma induced by ANIT.

TABLE 2

Changes of AST, ALT and ALP in mouse plasma of each group

| Group | AST (U/l) | ALT (U/l) | ALP (U/l) |
|---|---|---|---|
| Blank group | 43.0 ± 2.1 | 33.2 ± 4.6 | 20.0 ± 3.5 |
| ANIT model group | 1869.2 ± 582.5** | 1366.7 ± 548.3** | 333.6 ± 63.2** |
| Treatment group | 72.0 ± 34.4## | 54.0 ± 36.4## | 27.3 ± 3.7## |

Note: as comparing the model group with the blank group, **P < 0.01; as comparing the treatment group with the model group, ##P < 0.01.

Figure 1D:
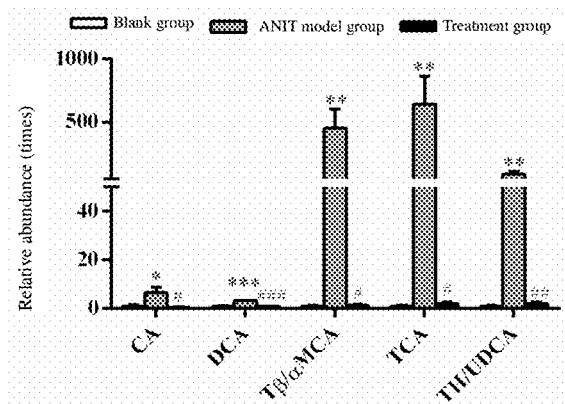

The relative content changes of various bile acid components in mouse plasma of each group were shown in FIG. 1D. The results showed that the levels of various bile acids in plasma of the treated group, such as CA, DCA, TβMCA/TαMCA, TCA, THDCA/TUDCA, were significantly lower than those of the ANIT model group.

Figure 1E:
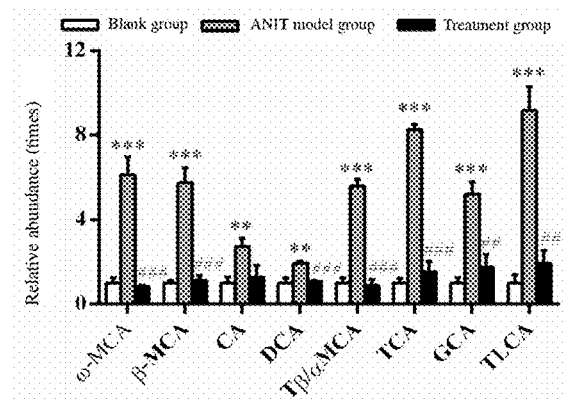

The relative content changes of various bile acid components in mouse liver of each group were shown in FIG. 1E. The results showed that the levels of various bile acids in liver of the treated group, such as ω-MCA, β-MCA, CA, DCA, TβMCA/TαMCA, TCA, GCA, TLCA were significantly lower than those of the ANIT model group. The above results indicated that celastrol could significantly inhibit the content increases of bile acid components in mouse plasma and liver induced by ANIT.

The above experimental results showed that celastrol had prevention and/or protection effects on ANIT-induced cholestatic liver injury, was capable of inhibiting the severe inflammatory infiltration and periportal hemorrhage induced by ANIT, inhibiting the increases of the levels of AST, ALT and ALP in mouse plasma induced by ANIT, and inhibiting the increases of the levels of bile acids in plasma and liver induced by ANIT.

Example 2: Prevention and/or Protection Effects of Celastrol on TAA-Induced Mouse Cholestasis Liver Disease 2.1 Experimental Animals C57BL/6 mice, SPF grade, body weight 20-23 g, male; certificate number: SCXK (Xiang) 2013-0004, purchased from Hunan SJA Laboratory Animal Co., Ltd.

2.2 Drugs and Reagents

Celastrol, red amorphous crystalline powder, Chengdu Ruifensi Biotechnology Co., Ltd., Lot No. L-003-150420.

Aspartate aminotransferase (AST) kit (Cat. No. C010-3, Lot No. 20161031), alanine aminotransferase (ALT) kit (Cat. No. C009-3, Lot No. 20161031) and alkaline phosphatase (ALP) kit (Cat. No. A059-3, Lot No. 20161031), produced by Nanjing Jiancheng Bioengineering Institute.

Thioacetamide (TAA, Cat. No. C1290-25G, Lot No. 1002213299), DMSO (Cat. No. V900090-500m1, Lot No. 101669350), Tween 80 (Cat. No. P1754-500m1, Lot No. 101761909), formic acid (Cat. No. 94318-250m1-F, Lot No. 101721592), chlorpropamide (Cat. No. C1290-25G, Lot No. 1002213299), cholic acid (CA, Cat. No. C1129-25G), deoxycholic acid (DCA, Cat. No. D2510-10G), taurocholic acid (TCA, Cat. No. T4009-1G), glycocholic acid (GCA, Cat. No. G2878-500MG), taurohyodeoxycholic acid (THDCA, Cat. No. T0682-250MG), taurochenodeoxycholic acid (TCDCA, Cat. No. T6260-25MG), taurodeoxycholate acid (TDCA, Cat. No. T0875-1G) and taurolithocholic acid (TLCA, Cat. No. T7515-100MG), purchased from Sigma Co.

Chromatographic grade acetonitrile (Cat. No. 1.00030.4008), purchased from Merck Co.

NaCl injection (Lot No. B16080E1), purchased from Zhejiang Guojing Pharmaceutical Co., Ltd.

ω-muricholic acid (ω-MCA, Cat. No. sc-396738) and tauro-β-muricholic acid (TβMCA, Cat. No. SC-361829), purchased from Santa Cruz Co.

Tauroursodeoxycholic acid (TUDCA, Cat. No. HY-19696A), purchased from MCE Co.

β-muricholic acid (β-MCA, Cat. No. C008852) and tauro-α-muricholic acid (TαMCA, Cat. No. C1893-000), purchased from Steraloids Co.

2.3 Main Instruments

Precision electronic balance, purchased from Sartorius Co.

Automatic microplate reader, purchased from BioTek Instruments Co.

SHA-C water bath constant temperature shaker, purchased from Changzhou Zhongcheng Instrument Manufacturing Co., Ltd.

Refrigerated centrifuge, purchased from Eppendorf Co.

Ultra-Performance Liquid Chromatography Quadrupole Time-of-Flight Mass Spectrometry, including 1290 sample injector, 1290 pump, column oven, XDB-C18 column (2.1× 100 mm, 1.8 μM), and 6530 quadrupole time-of-flight mass spectrometry, purchased from Agilent Co.

Precellys 24 tissue homogenizer, purchased from Bertin Technologies Co.

Upright microscope, purchased from Nikon Co.

Tissue microtome, purchased from Leica Co.

2.4 Experimental Methods 2.4.1 Experimental Grouping

A total of 18 male C57BL/6 mice were divided into three groups: blank group (n=6); model group (n=6); treatment group (n=6).

2.4.2 Preparation and Dosage of Drug Solution

Celastrol was dissolved in a solvent to obtain a solution of celastrol at a concentration of 2 mg/mL, wherein the solvent consisted of 1% DMSO, 2% Tween, and 97% water (v:v:v). For intragastrical administration, the dosage of celastrol was 10 mg/kg·d. TAA was dissolved in 0.9% NaCl solution to prepare a NaCl solution of TAA at a concentration of 60 mg/kg, and the dosage of TAA for intraperitoneal administration was 300 mg/kg.

2.4.3 Experimental Procedure

The treatment group was administered intragastrically with the celastrol solution at a dosage of 10 mg/kg·d for 4 consecutive days. At the same time, the blank group and the model group were intragastrically administered with the same dosage of a solvent, wherein the solvent consisted of 1% DMSO, 2% Tween 80 and 97% water (v:v:v), and the solvent was administrated for 4 consecutive days.

On the $4^{th}$ day, TAA model was established. 1 Hour after administration with the solvent or celastrol solution, the mice of the treatment group and the model group were respectively intraperitoneally injected with the NaCl solution of TAA at a dosage of 300 mg/kg to induce cholestatic liver injury. 24 Hours after treatment with TAA, the mice were sacrificed by $CO_2$ anesthesia, and plasma samples and liver samples were collected. The eyeballs of the mice were taken for blood collection. The plasma samples were placed on ice for 1-2 hours, centrifuged at 4000 g for 5 minutes at 4° C., and the supernatant plasma samples were taken to determine the plasma biochemical indicators, the levels of ALT, AST and ALP.

At the same time, plasma samples were prepared: 10 μL of plasma sample was taken, mixed with 190 μL of 67% acetonitrile (containing 5 μM internal standard chlorpropamide), centrifuged at 18000 g for 20 minutes at 4° C., and the supernatant was taken for sample injection.

Liver samples were prepared: 100 mg liver samples were mixed well with 1 mL of 50% acetonitrile (containing 5 μM internal standard chlorpropamide), shaken for 20 minutes at room temperature, and then centrifuged at 18000 g for 20 minutes at 4° C. Thereafter, 200 μL of the supernatant was taken and added with 200 μl of pure acetonitrile, vortexed for 1 minute, centrifuged at 18000 g for 20 minutes at 4° C., and the supernatant was taken for sample injection. The liquid chromatography conditions were as follows: the injection volume was 5 μL; the temperature of column was 45° C.; the flow rate of mobile phase was 0.3 mL/min; the gradient elution was that acetonitrile concentration changed from 2% to 98% during 16 minutes of operation, wherein the mobile phase (water/acetonitrile solution) contained 0.01% formic acid. The elution procedure was as follows: during $0\text{-}12^{th}$ minute, the acetonitrile concentration changed from 2% to 98% at a constant rate; $12\text{-}14^{th}$ minute, the acetonitrile concentration was maintained at 98%; $14\text{-}14.1^{th}$ minute, the acetonitrile concentration changed from 98% to 2%; $14.1\text{-}16^{th}$ minute, the acetonitrile concentration was maintained at 2%. Mass spectrometry conditions were as follows: the temperature of dry gas was 350° C., the pressure of nebulizer was 35 psi, and the voltage of capillary was 3.5 kV.

Part of the collected mouse liver tissue was fixed overnight in formalin and tissue sections were stained with hematoxylin and eosin (H&E).

2.5 Experimental Results

Figure 2A:
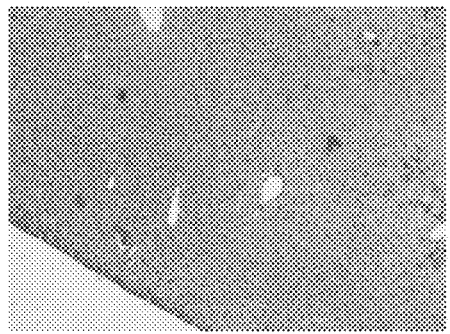
Figure 2B:
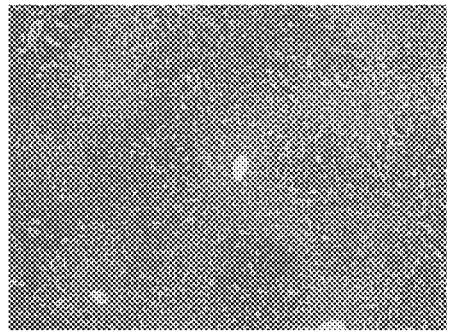
Figure 2C:
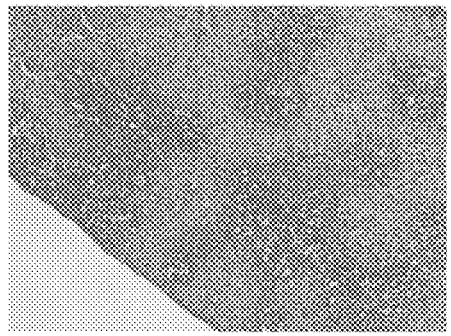

The H&E staining results of mouse liver tissues of each group were shown in FIG. 2A, FIG. 2B, and FIG. 2C. The results showed that the mouse liver tissue of the blank group had no damage, and severe necrosis of liver cells occurred in the liver tissue of the model group, while the area of liver necrosis in the liver tissue of the treatment group was significantly reduced. The results showed that celastrol could significantly inhibit the severe necrosis of liver cells induced by TAA.

The changes in body weight and liver weight of mouse in each group were shown in Table 3. The results showed that the mice in the blank group, the model group and the treatment group had uniform body weight, and there was no significant difference. However, the liver weight (1.54 g) of the model group was significantly higher than that (1.18 g) of the blank group, and the liver weight/body weight ratio (6.37%) of the model group was significantly higher than that (4.92%) of the blank group, indicating the mice of the TAA model had severe liver injury. When the mice were sacrificed, there was no significant difference in liver weight (1.55 g) of the treatment group in comparison with the model group; and there was no significant difference in the liver weight/body weight ratio of (6.48%) the treatment group in comparison with the model group, indicating that the prevention and/or protection effects of celastrol had no significant influence on liver weight in the mice of the TAA model.

TABLE 3

Changes in body weight and liver weight of mouse in each group

| Group | Body weight of mouse when sacrificed (g) | Liver weight of mouse when sacrificed (g) | Liver weight/body weight (%) |
|---|---|---|---|
| Blank group | 24.02 ± 1.09 | 1.18 ± 0.09 | 4.92 ± 0.38 |
| TAA model group | 24.10 ± 0.75 | 1.54 ± 0.18** | 6.37 ± 0.62** |
| Treatment group | 23.92 ± 0.63 | 1.55 ± 0.21 | 6.48 ± 0.93 |

Note: as comparing the model group with the blank group, **P < 0.01.

The changes of AST, ALT and ALP in mouse plasma of each group were shown in Table 4. The results showed that the levels of AST, ALT and ALP in plasma of the TAA model group were significantly higher than those of the blank group (P<0.05), indicating that a severe liver injury occurred in the TAA model group. The levels of AST, ALT and ALP of the treatment group were lower than those of the model group (P<0.01), indicating that celastrol could significantly inhibit the increases of the levels of AST, ALT and ALP in plasma induced by TAA.

TABLE 4

Changes of AST, ALT and ALP in mouse plasma of each group

| Group | AST (U/l) | ALT(U/l) | ALP(U/l) |
|---|---|---|---|
| Blank group | 81.7 ± 45.0 | 8.0 ± 4.2 | 101.6 ± 13.0 |
| TAA model group | 2204.4 ± 172.0** | 1407.5 ± 350.1** | 121.9 ± 11.1* |
| Treatment group | 920.3 ± 433.4## | 333.3 ± 211.3## | 50.1 ± 7.8## |

Note: as comparing the model group with the blank group, *P < 0.05, **P < 0.01; as comparing the treatment group with the model group, ##P < 0.01.

Figure 2D:
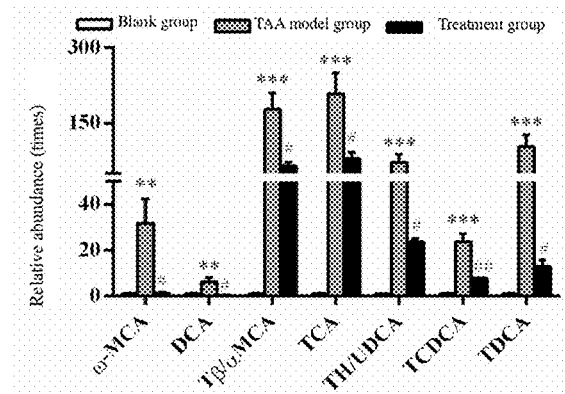

The relative content changes of various bile acid components in mouse plasma of each group were shown in FIG. 2D. The results showed that the levels of various bile acids in mouse plasma of the treatment group, such as ω-MCA, DCA, TβMCA/TαMCA, TCA, THDCA/TUDCA, TCDCA, TDCA, were significantly lower than those of the TAA model group.

Figure 2E:
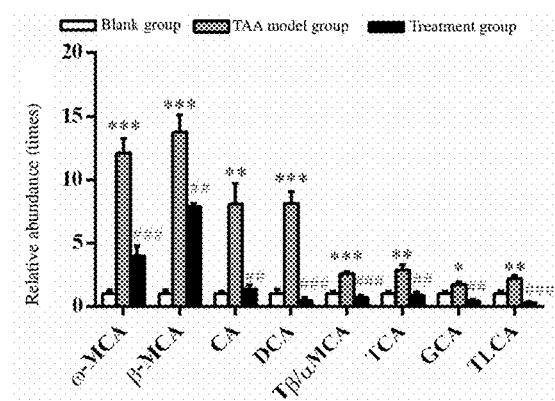

The relative content changes of various bile acid components in mouse liver of each group were shown in FIG. 2E. The results showed that the levels of various bile acids in mouse liver of the treatment group, such as ω-MCA, β-MCA, CA, DCA, TβMCA/TαMCA, TCA, GCA, TLCA, were significantly lower than those of the TAA model group. The above results indicated that celastrol could significantly inhibit the content increases of bile acid components in mouse plasma and liver induced by TAA.

The above experimental results showed that celastrol had prevention and/or protection effects on TAA-induced cholestatic liver injury, was capable of inhibiting the severe inflammatory infiltration and periportal hemorrhage induced by TAA, inhibiting the increases of the levels of AST, ALT and ALP in mouse plasma induced by TAA, and inhibiting the increased bile acids levels in plasma and liver induced by TAA.

Example 3: Effect of Sirtuin 1 (SIRT1) on Celastrol Activity in ANIT Model 3.1 Experimental Animals C57BL/6 mice, SPF grade, body weight 20-23 g, male; certificate number: SCXK (Xiang) 2013-0004, purchased from Hunan SJA Laboratory Animal Co., Ltd.

3.2 Drugs and Reagents

Celastrol, red amorphous crystalline powder, purchased from Chengdu Ruifensi Biotechnology Co., Ltd., Lot No. L-003-150420.

EX527 (Selisistat, purchased from MedChem Express Co., Cat. No. HY-15453).

Aspartate aminotransferase (AST) kit (Cat. No. C010-3, Lot No. 20161031), alanine aminotransferase (ALT) kit (Cat. No. C009-3, Lot No. 20161031) and alkaline phosphatase (ALP) kit (Cat. No. A059-3, Lot No. 20161031), produced by Nanjing Jiancheng Bioengineering Institute.

α-Naphthyl isothiocyanate (ANIT, Cat. No. N4525-10G, Lot No. 101734146), DMSO (Cat. No. V900090-500m1, Lot No. 101669350), Tween 80 (Cat. No. P1754-500m1, Lot No. 101761909), formic acid (Cat. No. 94318-250m1-F, Lot No. 101721592), chlorpropamide (Cat. No. C1290-25G, Lot No. 1002213299), cholic acid (CA, Cat. No. C1129-25G), deoxycholic acid (DCA, Cat. No. D2510-10G), taurocholic acid (TCA, Cat. No. T4009-1G) and taurohyodeoxycholic acid (THDCA, Cat. No. T0682-250MG), purchased from Sigma Co.

Corn oil (Cat. No. C116025-500G, Lot No. 11524089), purchased from Aladdin Co.

Chromatographic grade acetonitrile (Cat. No. 1.00030.4008), purchased from Merck Co.

Tauro-β-muricholic acid (TβMCA, Cat. No. SC-361829), purchased from Santa Cruz Co.

Tauroursodeoxycholic acid (TUDCA, Cat. No. HY-19696A), purchased from MCE Co.

Tauro-α-muricholic acid (TαMCA, Cat. No. C1893-000), purchased from Steraloids Co.

3.3 Main Instruments

Precision electronic balance, purchased from Sartorius Co.

Automatic microplate reader, purchased from BioTek Instruments Co.

SHA-C water bath constant temperature shaker, purchased from Changzhou Zhongcheng Instrument Manufacturing Co., Ltd.

Refrigerated centrifuge, purchased from Eppendorf Co.

Ultra-Performance Liquid Chromatography Quadrupole Time-of-Flight Mass Spectrometry, including 1290 sample injector, 1290 pump, column oven, XDB-C18 column (2.1× 100 mm, 1.8 μM), and 6530 quadrupole time-of-flight mass spectrometry, purchased from Agilent Co.

Upright microscope, purchased from Nikon Co.
Tissue microtome, purchased from Leica Co.

3.4 Experimental Methods 3.4.1 Experimental Grouping

A total of 24 male C57BL/6 mice were divided into four groups: blank group (n=6); model group (n=6); treatment group (n=6); and EX527 group (n=6).

3.4.2 Preparation and Dosage of Drug Solution

Celastrol was dissolved in a solvent to obtain a celastrol solution at a concentration of 2 mg/mL, wherein the solvent consisted of 1% DMSO, 2% Tween 80, and 97% water (v:v:v). For intragastrical administration, the dosage of celastrol was 10 mg/kg·d. ANIT was dissolved in corn oil to obtain a corn oil solution of ANIT at a concentration of 15 mg/mL, and the dosage of ANIT for intragastrical administration was 75 mg/kg. EX527 was dissolved in corn oil to obtain a corn oil solution of EX527 at a concentration of 2 mg/mL, and the dosage of EX527 for intraperitoneal injection was 10 mg/kg·d.

3.4.3 Experimental Procedure

The EX527 group was simultaneously administered with the celastrol solution and the EX527 corn oil solution for 5 consecutive days. The treatment group was administered with the celastrol solution and an equal dosage of corn oil for 5 consecutive days. At the same time, the blank group and the model group were administered with equal dosages of solvent (1% DMSO, 2% Tween 80 and 97% water (v:v:v)) and corn oil, and the solvent was administered for 5 consecutive days.

On the $3^{rd}$ day of administration, ANIT model was established. 4 Hours after administration, the mice in the model group, the treatment group and the EX527 group were respectively intraperitoneally injected with the ANIT corn oil solution at a dosage of 75 mg/kg for single administration to induce cholestatic liver injury, and the blank group was fed with an equal dosage of corn oil. After the model was established on the $3^{rd}$ day of administration, the treatment group was continuously administered with celastrol, the EX527 group was continuously administered with celastrol and EX527, and the blank group and the model group were continuously administered with the same dosage of solvent. 48 Hours after administration with ANIT, the mice were sacrificed by $CO_2$ anesthesia, and mouse liver samples and plasma samples were taken. The eyeballs of the mice were taken for blood collection. The plasma samples were placed on ice for 1-2 hours, centrifuged at 4000 g for 5 minutes at 4° C., and the supernatants of the plasma samples were taken to determine plasma biochemical indicators, the levels of ALT, AST and ALP.

At the same time, plasma samples were prepared: 10 μL of plasma sample was taken, mixed well with 190 μL of 67% acetonitrile (containing 5 μM internal standard chlorpropamide), centrifuged at 18000 g for 20 minutes at 4° C., and the supernatant was taken for sample injection. The liquid chromatography conditions were as follows: the injection volume was 5 μL; the temperature of column was 45° C.; the flow rate of mobile phase was 0.3 mL/min; the gradient elution was that acetonitrile concentration changed from 2% to 98% during 16 minutes of operation, wherein the mobile phase (water/acetonitrile solution) contained 0.01% formic acid. The elution procedure was as follows: during 0-12$^{th}$ minute, the acetonitrile concentration changed from 2% to 98% at a constant rate; during 12-14$^{th}$ minute, the acetonitrile concentration was maintained at 98%; during 14-14.1$^{th}$ minute, the acetonitrile concentration changed from 98% to 2%; during 14.1-16$^{th}$ minute, the acetonitrile concentration was maintained at 2%. Mass spectrometry conditions were as follows: the temperature of dry gas was 350° C., the pressure of nebulizer was 35 psi, and the voltage of capillary was 3.5 kV.

Part of the collected mouse liver tissue was fixed overnight in formalin and tissue sections were stained with hematoxylin and eosin (H&E).

3.5 Experimental Results

Figure 3A:
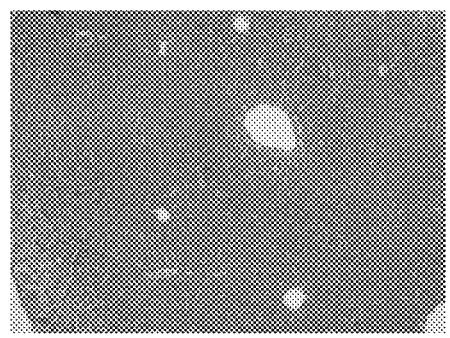
Figure 3B:
Figure 3C:
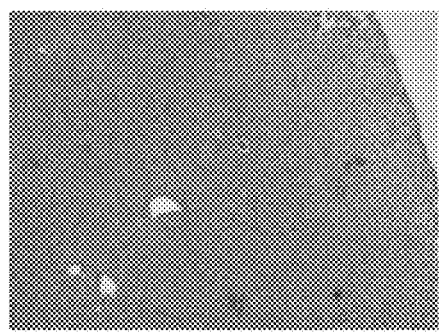
Figure 3D:
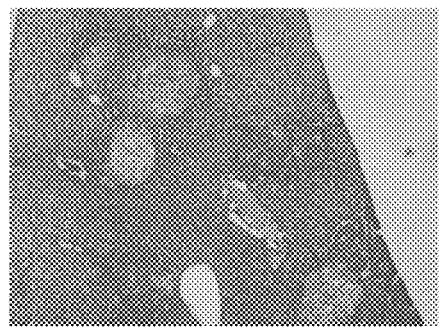

The H&E staining results of mouse liver were shown in FIG. 3A, FIG. 3B, FIG. 3C and FIG. 3D. The results showed that the liver tissue of the blank group had no damage, a severe inflammatory infiltration and a periportal hemorrhage occurred in the liver tissue of the model group, the mouse liver tissue of the treatment group had no obvious damage, and a severe inflammatory infiltration and a periportal hemorrhage also occurred in the mouse liver tissue of the EX527 group. The results showed that celastrol could significantly inhibit ANIT-induced severe inflammatory infiltration and periportal hemorrhage. In FIG. 3D, the mouse liver tissue section of the EX527 group showed inflammatory infiltration, indicating that the protection effect of celastrol was reduced after the administration with SIRT1 inhibitor EX527.

Figure 3E:
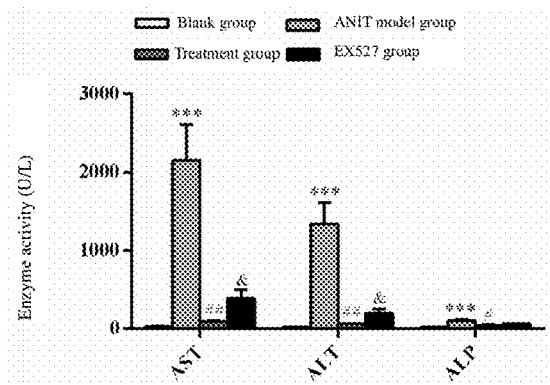

The changes of AST, ALT and ALP in mouse plasma of each group were shown in FIG. 3E. The results showed that the levels of AST, ALT and ALP in plasma of the model group were significantly higher than those of the blank group (P<0.001), indicating that the mice of model group had severe liver injury. The levels of AST, ALT and ALP of the treatment group were lower than those of the model group (P<0.05), indicating that celastrol could significantly inhibit the increased level of AST, ALT and ALP in mouse plasma induced by ANIT. The levels of AST and ALT in plasma of the EX527 group were significantly higher than those of the treatment group (P<0.05), indicating that the protection effect of celastrol was reduced after the administration with SIRT1 inhibitor EX527.

Figure 3F:
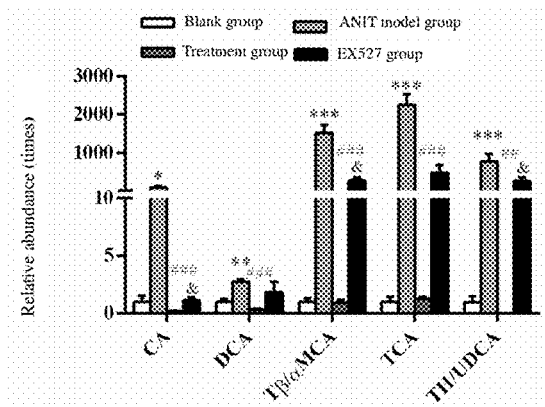

The relative content changes of various bile acid components in mouse plasma of each group were shown in FIG. 3F. The results showed that the levels of various bile acids in plasma of the treatment group, such as CA, DCA, TβMCA/TαMCA, TCA, THDCA/TUDCA, were significantly lower than those of the model group, indicating that celastrol could significantly inhibit the increases of the levels of various bile acids in mouse plasma induced by ANIT. The levels of CA, TβMCA/TαMCA and THDCA/TUDCA in mouse plasma of the EX527 group were significantly higher than those of the treatment group (P<0.05), indicating that the protective effect of celastrol on liver was reduced after the administration with SIRT1 inhibitor EX527.

Example 4: Effect of SIRT1 on Celastrol Activity in TAA Model

4.1 Experimental Animals

C57BL/6 mice, SPF grade, body weight 20-23 g, male; certificate number: SCXK (Xiang) 2013-0004, purchased from Hunan SJA Laboratory Animal Co., Ltd.

4.2 Drugs and Reagents

Celastrol, red amorphous crystalline powder, Chengdu Ruifensi Biotechnology Co., Ltd., Lot No. L-003-150420.

EX527 (Selisistat, purchased from MedChem Express Co., Cat. No. HY-15453).

Aspartate aminotransferase (AST) kit (Cat. No. C010-3, Lot No. 20161031), alanine aminotransferase (ALT) kit (Cat. No. C009-3, Lot No. 20161031) and alkaline phosphatase (ALP) kit (Cat. No. A059-3, Lot No. 20161031), produced by Nanjing Jiancheng Bioengineering Institute.

Thioacetamide (TAA, Cat. No. C1290-25G, Lot No. 1002213299), DMSO (Cat. No. V900090-500m1, Lot No. 101669350), Tween 80 (Cat. No. P1754-500m1, Lot No. 101761909), formic acid (Cat. No. 94318-250m1-F, Lot No. 101721592), chlorpropamide (Cat. No. C1290-25G, Lot No. 1002213299), deoxycholic acid (DCA, Cat. No. D2510-10G), taurocholic acid (TCA, Cat. No. T4009-1G), taurohyodeoxycholic acid (THDCA, Cat. No. T0682-250MG), taurochenodeoxycholic acid (TCDCA, Cat. No. T6260-25MG) and taurodeoxycholic acid (TDCA, Cat. No. T0875-1G), purchased from Sigma Co.

Chromatographic grade acetonitrile (Cat. No. 1.00030.4008), purchased from Merck Co.

NaCl injection (Lot No. B16080E1), purchased from Zhejiang Guojing Pharmaceutical Co., Ltd.

ω-muricholic acid (ω-MCA, Cat. No. sc-396738) and tauro-β-muricholic acid (TβMCA, Cat. No. SC-361829), purchased from Santa Cruz Co.

Tauroursodeoxycholic acid (TUDCA, Cat. No. HY-19696A), purchased from MCE Co.

Tauro-α-muricholic acid (TαMCA, Cat. No. C1893-000), purchased from Steraloids Co.

4.3 Main Instruments

Precision electronic balance, purchased from Sartorius Co.

Automatic microplate reader, purchased from BioTek Instruments Co.

SHA-C water bath constant temperature shaker, purchased from Changzhou Zhongcheng Instrument Manufacturing Co., Ltd.

Refrigerated centrifuge, purchased from Eppendorf Co.

Ultra-Performance Liquid Chromatography Quadrupole Time-of-Flight Mass Spectrometry, including 1290 sample injector, 1290 pump, column oven, XDB-C18 column (2.1× 100 mm, 1.8 μM), and 6530 quadrupole time-of-flight mass spectrometry, purchased from Agilent Co.

Upright microscope, purchased from Nikon Co.

Tissue microtome, purchased from Leica Co.

4.4 Experimental Methods

4.4.1 Experimental Grouping

A total of 24 male C57BL/6 mice were divided into four groups: blank group (n=6); model group (n=6); treatment group (n=6); EX527 group (n=6).

4.4.2 Preparation and Dosage of Drug Solution

Celastrol was dissolved in a solvent to obtain a solution of celastrol at a concentration of 2 mg/mL, wherein the solvent consisted of 1% DMSO, 2% Tween, and 97% water (v:v:v). For intragastrical administration, the dosage of celastrol was 10 mg/kg·d. TAA was dissolved in 0.9% NaCl solution to prepare a NaCl solution of TAA at a concentration of 60 mg/mL, and the dosage of TAA for intraperitoneal administration was 300 mg/kg. EX527 was dissolved in corn oil to prepare a corn oil solution of EX527 at a concentration of 2 mg/mL, and the dosage of EX527 for intraperitoneal administration was 10 mg/kg. d.

4.4.3 Experimental Procedure

The EX527 group was simultaneously administered with the celastrol solution and the EX527 corn oil solution for 4 consecutive days. The treatment group was administrated with the celastrol solution and an equal dosage of corn oil for 4 consecutive days. At the same time, the blank group and the model group were administrated with equal dosages of solvent (1% DMSO, 2% Tween 80 and 97% water (v:v:v)) and corn oil, and the solvent was administered for 4 consecutive days.

On the $4^{th}$ day, the establishment of TAA model was performed. 1 Hour after administration, the mice in the model group, the treatment group and the EX527 group were intraperitoneally injected with TAA at a dosage of 300 mg/kg to induce cholestatic liver injury. 24 Hours after administration with TAA, the mice were sacrificed by $CO_2$ anesthesia, and plasma samples and liver samples were collected. The eyeballs of the mice were taken for blood collection. The plasma samples were placed on ice for 1-2 hours, centrifuged at 4000 g for 5 minutes at 4° C., and the supernatants of plasma samples were taken to determine the plasma biochemical indicators, the levels of ALT, AST, and ALP.

At the same time, plasma samples were prepared: 10 μL of plasma sample was mixed with 190 μL of 67% acetonitrile (containing 5 μM internal standard chlorpropamide), centrifuged at 18000 g for 20 minutes at 4° C., and the supernatant was taken for sample injection. The liquid chromatography conditions were as follows: the volume of injection was 5 μL; the temperature of column was 45° C.; the flow rate of mobile phase was 0.3 mL/min; the gradient elution was that acetonitrile concentration changed from 2% to 98% during 16 minutes of operation, wherein the mobile phase (water/acetonitrile solution) contained 0.01% formic acid. The elution procedure was as follows: during 0-12$^{th}$ minute, the acetonitrile concentration changed from 2% to 98% at a constant rate; during 12-14$^{th}$ minute, the acetonitrile concentration was maintained at 98%; during 14-14.1$^{th}$ minute, the acetonitrile concentration changed from 98% to 2%; during 14.1-16$^{th}$ minute, the acetonitrile concentration was maintained at 2%. Mass spectrometry conditions were as follows: the temperature of dry gas was 350° C., the pressure of nebulizer was 35 psi, and the voltage of capillary was 3.5 kV.

Part of the collected mouse liver tissue was fixed overnight in formalin, and tissue sections were stained with hematoxylin and eosin (H&E).

4.5 Experimental Results

Figure 4A:
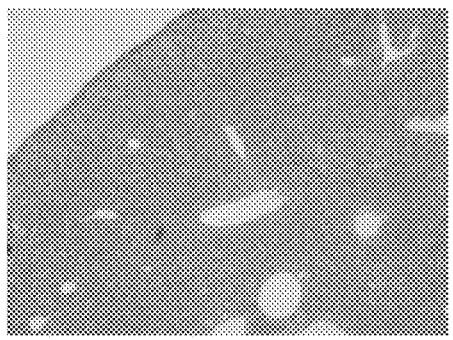
Figure 4B:
Figure 4C:
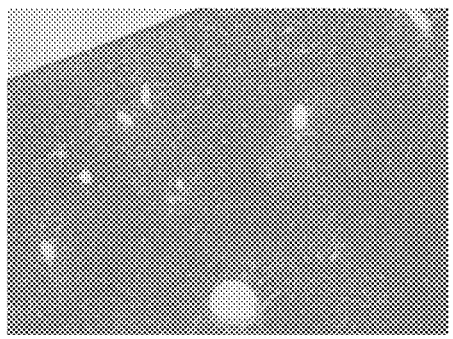
Figure 4D:

The H&E staining results of mouse liver tissues of each group were shown in FIG. 4A, FIG. 4B, FIG. 4C, and FIG. 4D. The results showed that the mouse liver tissue of the blank group had no damage, a severe necrosis of liver cells occurred in the mouse liver tissue of the model group, the area of necrosis of liver cells in the mouse liver tissue of the treatment group was significantly reduced, and a severe necrosis of liver cells also occurred in the mouse liver tissue of the EX527 group, which indicated that celastrol could significantly inhibit severe necrosis of liver cells induced by TAA. In FIG. 4D, the mouse liver tissue section of the EX527 group showed severe necrosis of liver cells, indicating that the protection effect of celastrol in the mice was reduced after the administration with SIRT1 inhibitor EX527.

Figure 4E:
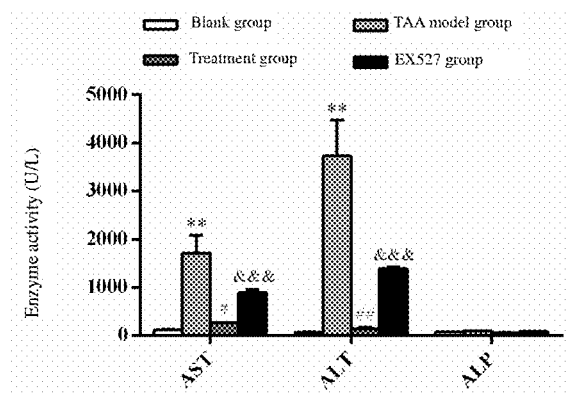

The changes of AST, ALT, and ALP in mouse plasma of each group were shown in FIG. 4E. The results showed that the levels of AST and ALT in plasma of the model group were significantly higher than those of the blank group (P<0.01), indicating that the mice of the model group had severe liver injury. The levels of AST and ALT of the treatment group were lower than those of the model group (P<0.05), indicating that celastrol could significantly inhibit the increases of the levels of AST and ALT in plasma induced by TAA. The levels of AST and ALT in plasma of the EX527 group were significantly higher than those of the treatment group (P<0.001), indicating that the protection of celastrol was reduced after the administration with SIRT1 inhibitor EX527 in the mice.

Figure 4F:
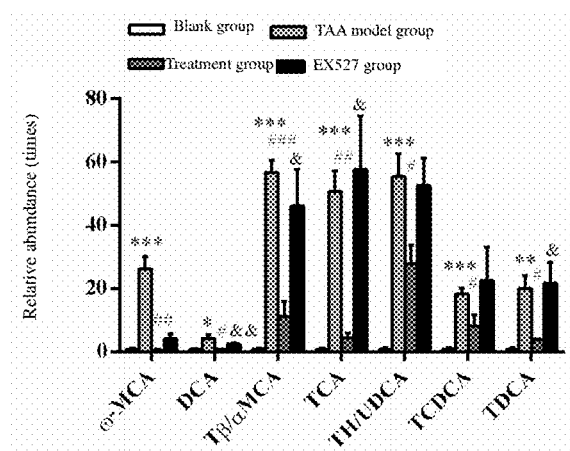

The relative content changes of various bile acid components in mouse plasma of each group were shown in FIG. 4F. The results showed that the levels of various bile acids in mouse plasma of the treatment group, such as ω-MCA, DCA, TβMCA/TαMCA, TCA, THDCA/TUDCA, TCDCA, TDCA, were significantly lower than those of the TAA model group (P<0.05), indicating that celastrol could significantly inhibit the increases of the levels of various bile acids in mouse plasma induced by TAA. The levels of DCA, TβMCA/TαMCA, TCA and TDCA in mouse plasma of the EX527 group were significantly higher than those of the treatment group (P<0.05), indicating that the protection effect of celastrol on liver was reduced after the administration with SIRT1 inhibitor EX527 in the mice.

Example 5: Effect of Farnesoid X Receptor (FXR) on Celastrol Activity in ANIT Model The same experimental method of Example 1 was used, wherein the experimental animals were FXR knockout mice (C57BL/6J as background), and the FXR knockout mice were presented by Frank J. Gonzalez, a researcher of the Cancer Institute of National Institutes of Health, USA.

The changes of AST, ALT, and ALP in plasma of FXR knockout mice of each group were shown in FIG. 5A. The results showed that the levels of AST, ALT, and ALP in plasma of the model group were significantly higher than those of the blank group (P<0.01), indicating that a severe liver injury occurred in mice of the model group mice. The levels of ALT and ALP of the treatment group showed no significant decrease in comparison with the model group, indicating that the protection effect of celastrol on liver was weakened under FXR knockout conditions.

The relative content changes of various bile acid components in plasma of FXR knockout mice of each group were shown in FIG. 5B. The results showed that the levels of various bile acids in the treatment group, such as CA, DCA, TβMCA/TαMCA, TCA, THDCA/TUDCA, showed no significant decrease in comparison with the ANIT model group, indicating that the protection effect of celastrol on liver was weakened under FXR knockout condition.

Example 6: Effect of FXR on Celastrol Activity in TAA Model

The same experimental method of Example 2 was used, wherein the experimental animals were FXR knockout mice (C57BL/6J as background), and the FXR knockout mice were presented by Frank J. Gonzalez, a researcher of the Cancer Institute of National Institutes of Health, USA.

The H&E staining results of liver tissue of FXR knockout mice of each group were shown in FIG. 6A, FIG. 6B and FIG. 6C. The results showed that the liver tissue of the blank group had no damage, a severe necrosis of liver cells occurred in the liver tissue of the model group, and a severe necrosis of liver cells also occurred in the liver tissue of the treatment group, indicating that under FXR knockout mice condition, celastrol could not significantly inhibit the severe necrosis of liver cells induced by TAA.

The changes of AST, ALT, and ALP in plasma of FXR knockout mice of each group were shown in FIG. 6D. The results showed that the levels of AST, ALT, and ALP in plasma of the model group were significantly higher than those of the blank group ($P<0.001$), indicating that the model group had severe liver injury. The level of AST of the treatment group showed no significant decrease in comparison with the model group, indicating that the protection effect of celastrol on liver was weakened under FXR knockout condition.

The relative content changes of various bile acid components in plasma of FXR knockout mice of each group were shown in FIG. 6E. The results showed that the levels of various bile acids in the treatment group, such as co-MCA, DCA, TCA, THDCA/TUDCA, TCDCA, showed no significant decrease in comparison with the ANIT model group, indicating the protection effect of celastrol on liver was weakened under FXR knockout condition.

Example 7: Therapeutic Effect of Celastrol on TAA-Induced Liver Fibrosis in Mice 7.1 Experimental Animals: C57BL/6 Mice, SPF Grade, Body Weight 20-23 g, Male; Certificate Number: SCXK (Xiang) 2013-0004, Purchased from Hunan SJA Laboratory Animal Co., Ltd 7.2 Drugs and Reagents Celastrol, red amorphous crystalline powder, purchased from Chengdu Ruifensi Biotechnology Co., Ltd., Lot No. L-003-150420.

Aspartate aminotransferase (AST) kit (Cat. No. C010-3, Lot No. 20161031), alanine aminotransferase (ALT) kit (Cat. No. C009-3, Lot No. 20161031), and alkaline phosphatase (ALP) kit (Cat. No. A059-3, Lot No. 20161031), produced by Nanjing Jiancheng Bioengineering Institute.

Thioacetamide (TAA, Cat. No. C1290-25G, Lot No. 1002213299), DMSO (Cat. No. V900090-500m1, Lot No. 101669350) and Tween 80 (Cat. No. P1754-500m1, Lot No. 101761909), purchased from Sigma Co.

NaCl injection (Lot No. B16080E1), purchased from Zhejiang Guojing Pharmaceutical Co., Ltd.

7.3 Main Instruments: Precision Electronic Balance, Purchased from Sartorius Co.; Automatic Microplate Reader, Purchased from BioTek Instruments Co.; SHA-C Water Bath Constant Temperature Shaker, Purchased from Changzhou Zhongcheng Instrument Manufacturing Co., Ltd.; Refrigerated Centrifuge, Purchased from Eppendorf Co.; Upright Microscope, Purchased from Nikon Co.; Tissue Microtome, Purchased from Leica Co 7.4 Experimental Method 7.4.1 Experimental Grouping A total of 30 male C57BL/6 mice were divided into three groups: blank group (n=10); TAA liver fibrosis group (n=10); treatment group (n=10).

7.4.2 Preparation and Dosage of Drug Solution

Celastrol was dissolved in a solvent to obtain a celastrol solution at a concentration of 2 mg/mL, wherein the solvent consisted of 1% DMSO, 2% Tween 80, and 97% water (v:v:v); for intragastrical administration, the dosage of celastrol was 10 mg/kg/time, three times per week, and the administration was absent in the first week. TAA was dissolved in 0.9% NaCl solution to prepare a NaCl solution of TAA at a concentration of 20 mg/kg, and the dosage for intraperitoneal administration was 100 mg/kg/time in the first week and 160 mg/kg/time in the second to sixth week, three times per week.

7.4.3 Experimental Procedure

The model group and the treatment group were administrated with TAA three times per week, and administered every other day. The dosage of TAA was 100 mg/kg each time during the first week. From the second week onwards, the dosage of TAA administered to the model group and the treatment group was changed to 160 mg/kg each time. The blank group was given an equal dosage of NaCl solution.

The treatment group was administrated with celastrol from the second week, in which celastrol at a dosage of 10 mg/kg was administered 1 hour after administration with TAA. The blank group and the model group were administrated with an equal dosage of solvent (1% DMSO, 2% Tween 80, and 97% water (v: v: v)).

Six weeks later, mice were sacrificed by $CO_2$ anesthesia, and mouse plasma samples and liver samples were collected. The eyeballs of the mice were taken for blood collection. The plasma samples were placed on ice for 1-2 hours, centrifuged at 4000 g for 5 minutes at 4° C., and the supernatants of plasma samples were taken to determine the plasma biochemical indicators, the levels of ALT, AST, and ALP.

Part of the collected mouse liver tissue was fixed overnight in formalin, and tissue sections were stained with hematoxylin and eosin (H&E).

7.5 Experimental Results

The H&E staining results of mouse liver tissue of each group were shown in FIG. 7A, FIG. 7B and FIG. 7C. The results showed that the mouse liver tissue of the blank group had no damage, a severe necrosis of liver cells occurred and the whole liver morphology changed in the mouse liver tissue of the model group, the mouse liver tissue damage of the treatment group was reduced and the liver morphology was also significantly recovered, indicating that celastrol could significantly reduce the TAA-induced severe necrosis of liver cells and liver fibrosis, and could significantly recover the whole liver morphology.

The changes of AST, ALT, and ALP in mouse plasma of each group were shown in FIG. 7D. The results showed that the levels of AST and ALT in plasma of the model group were significantly higher than those of the blank group ($P<0.01$), indicating that a severe liver fibrosis occurred in the model group mice. The levels of AST and ALT of the treatment group were significantly lower than those of the model group ($P<0.05$), indicating that celastrol could treat the TAA-induced liver fibrosis.

It should be noted that the above examples are only used to illustrate the technical solutions of the present disclosure and are not to be construed as limitation thereof; although the present disclosure will be described in detail with reference to the preferred examples, those skilled in the art should understand that the specific embodiments as disclosed can be amended and partial technical features of the present disclosure are can be replaced without departing from the spirit of the technical solution of the present disclosure, all these changes fall into the protection scope sought to be protected by the present application.

The invention claimed is:

1. A method for treatment of a cholestatic liver disease, the method comprising administering to a patient in need thereof a therapeutically effective amount of celastrol or a pharmaceutically acceptable salt thereof, or the method comprising administering to a patient in need thereof a therapeutically effective amount of a pharmaceutical composition, wherein the pharmaceutical composition comprises celastrol or a pharmaceutically acceptable salt thereof, and a pharmaceutically acceptable adjuvant or excipient.

2. The method according to claim 1, wherein the cholestatic liver disease is a chemical substance-induced cholestatic liver disease, a drug-induced cholestatic liver disease, a primary cholestatic liver disease or a cholestatic liver disease caused by excessive estrogen in vivo.

3. The method of claim 1, wherein the celastrol or a pharmaceutically acceptable salt thereof decreases bile acid components in a patient's plasma, or reduces liver injury, liver necrosis caused by cholestasis, or inhibits or alleviates inflammation caused by cholestasis.

4. The method of claim 3, wherein the bile acid component includes at least one component selected from the group consisting of: ω-MCA, DCA, TβMCA, TαMCA, TCA, THDCA, TUDCA, TCDCA, and TDCA.

* * * * *